United States Patent [19]

Fusayama et al.

[11] 4,443,197

[45] Apr. 17, 1984

[54] VARNISH FOR PROTECTING A TOOTH SURFACE

[75] Inventors: Takeo Fusayama, Tokyo; Junichi Yamauchi, Kurashiki, both of Japan

[73] Assignee: Kuraray Co., Ltd., Kurashiki, Japan

[21] Appl. No.: 471,849

[22] Filed: Mar. 3, 1983

[30] Foreign Application Priority Data

Mar. 12, 1982 [JP] Japan ................................. 57-39694

[51] Int. Cl.$^3$ .............................................. A61K 6/08
[52] U.S. Cl. ...................................... 433/217; 106/35; 260/998.11; 433/215; 433/226; 433/228; 523/115
[58] Field of Search .................. 106/35; 435/217, 215, 435/226, 227, 228; 523/115

[56] References Cited

U.S. PATENT DOCUMENTS

| | | | |
|---|---|---|---|
| 3,926,906 | 12/1975 | Lee et al. | 524/786 |
| 4,148,988 | 4/1979 | Masuhara et al. | 106/35 |
| 4,182,035 | 1/1980 | Yamauchi et al. | 433/228 |
| 4,222,780 | 9/1980 | Shibatani et al. | 106/35 |
| 4,259,075 | 3/1981 | Yamauchi et al. | 106/35 |
| 4,259,117 | 3/1981 | Yamauchi et al. | 106/35 |
| 4,302,381 | 11/1981 | Omura et al. | 523/116 |
| 4,347,174 | 8/1982 | Nagase et al. | 523/116 |

*Primary Examiner*—Lorenzo B. Hayes
*Attorney, Agent, or Firm*—Oblon, Fisher, Spivak, McClelland & Maier

[57] ABSTRACT

A varnish for the formation of a coating layer on a tooth surface to protect healthy tooth surface against the erosion by an acid etching solution during tooth restoration which comprises a polymer comprising vinyl chloride and vinyl acetate as the main monomer units dissolved in a dentally acceptable solvent.

11 Claims, No Drawings

VARNISH FOR PROTECTING A TOOTH SURFACE

BACKGROUND OF THE INVENTION

1. Field of the Invention

This invention relates to a method for protecting healthy tooth surfaces against erosion by an acid etching agent utilized in tooth restoration treatments and to a varnish for forming a temporary coated layer on tooth surfaces during said treatment.

2. Description of the Prior Art

A method which has been widely used in the past for restoring teeth comprises removing the caries portion of the tooth and filling the cavity with a composite resin to restore the tooth. In this method, adhesion of the composite resin to the tooth is a problem, and if the adhesion is poor, the filling falls from the tooth or further caries development occurs between the tooth and the filling. For this reason, it is necessary to improve the adhesion between resin and cavity surfaces, and it is common practice to treat the tooth surface with an acid etching agent comprising an aqueous solution of phosphoric acid, citric acid or the like and further coating the surfaces of the cavity with a bonding agent containing an adhesive monomer before filling the cavity with the composite resin [J. Dent. Res., 34, 849 (1955), U.S. Pat. No. 4,259,075]. Although the acid etching agent is effective in promoting enhanced adhesion between the composite resin and the surfaces of the cavity by providing a minutely irregular tooth surface, the method has the disadvantage that, if the acid treating agent spreads over into healthy tooth surfaces, it also etches the healthy tooth surfaces (especially the enamel) thereby forming an irregular etched surface upon which dental plaque forms and to which the bacteria cling, thus leading to the formation of caries. In order to prevent this situation, the viscosity of the acid etchant has been increased in order to limit the flow and spread of the etchant to adjacent areas by adding carboxy-methyl cellulose or highly dispersed, submicron size silica to the acid aqueous solution (Japanese Patent application Laid-Open No. 36994/1978). However, such an etchant is difficult to apply to only the caries portion of the tooth, and therefore it is difficult, if not impossible, to avoid the spreading of the acid etchant to nearby healthy tooth surfaces. A need therefore continues to exist for an improved method of applying and acid etchants to restricted areas of tooth surfaces.

SUMMARY OF THE INVENTION

Accordingly, one object of the present invention is to provide a method for restoring teeth while preventing the erosion of healthy tooth surfaces with an acid etching agent by temporarily protecting the healthy tooth surfaces and to provide a varnish which forms a temporary coated layer on the tooth surfaces to be protected during said restoration process.

Briefly, this object and other objects of the present invention as hereinafter will become more readily apparent can be attained by a method of restoring a carious tooth by applying a polymer solution to the tooth surface, and evaporating the solvent from said solution to form a polymer coating on the tooth surface, removing the carious portion of the tooth by drilling, applying an acid etching agent to the walls of the tooth cavity from which the carious material has been removed, filling the tooth cavity with a dental filling material and removing the polymer coating from the healthy tooth surfaces.

DETAILED DESCRIPTION OF THE PREFERRED EMBODIMENTS

The polymer coating of the present invention which is formed on tooth surfaces must exhibit the characteristics of being stable by properly adhering to the tooth so that when an acid etching agent is applied to the surface of a tooth cavity from which the caries portion has been removed, the acid etching agent does not spread over to the healthy tooth surfaces, and at the same time being easily cut when the caries portion of the tooth is removed by drilling, so that only the coating on the surface of the caries is removed and the coating on the healthy tooth surface remains intact. Further, the polymer coating on the tooth surface should desirably be removable by the simple operation of polishing. Therefore, the polymer solution of the present invention which is applied to tooth surfaces is a solution which contains a polymer which exhibits the above-described characteristics and which is harmless to the human body. In a preferred embodiment of the invention, the polymer is composed of vinyl chloride and vinyl acetate as the main monomeric ingredients dissolved in a solvent. From the point of view of improvement in the tackiness of the applied coating to the enamel of the tooth, the polymer should contain a small amount of carboxylic acid or carboxylic acid anhydride groups. Accordingly, the polymer desirably should comprise a mixture of a copolymer (A) of (a) vinyl chloride and (b) vinyl acetate and a copolymer (B) of (a) vinyl chloride, (b) vinyl acetate, and (c) a vinyl compound having a carboxylic acid or carboxylic acid anhydride group or groups. Suitable copolymers (A) and (B) are known polymers employed in the manufacture of paints, coating materials and the like which are applied to plastics, metals, cements and the like. Such polymers are described in, for example, Japanese Patent Publication No. 17505/1968, Japanese Patent application Laid-open No. 61235/1979, Canadian Patent 745,215. Of course, the use of such polymers for the purposes of the present invention is not disclosed in any of these references.

In the present invention, the compositional ratio of vinyl chloride to vinyl acetate in copolymers (A) and (B) is preferably 95–60:5–40 mole %, more preferably 90–72:10–28 mole %. If the content of the vinyl chloride components exceeds 95 mole %, the tackiness of the varnish to the enamel is poor, whereas if the vinyl acetate component is more than 40 mole %, the coating to a significant extent breaks off from the tooth enamel surface where it should be retained when the caries portion is removed by using a bar, as described hereinbelow. In copolymer (B), the vinyl compound having a carboxylic acid or carboxylic acid anhydride group or groups is preferably present in the copolymer in an amount of 1–20 mole %, more preferably 2–10 mole %, based on the content of the vinyl chloride and vinyl acetate. By the presence of an appropriate amount of said carboxylic acid or acid anhydride group or groups, the tackiness of the copolymer composition to the enamel is further enhanced. Suitable examples of such carboxylic group containing compounds include acrylic acid, methacrylic acid, maleic acid, fumaric acid, itaconic acid, crotonic acid and acid anhydrides thereof. In the present invention, the relative amounts of copolymer (A) and copolymer (B) preferably range from 95–40 and 5–60% by weight, more preferably 90–60 and 10–40% by weight, respectively. If too great an amount of copolymer (B) is present, there is a tendency for the coating to become hard and brittle. Further, both copolymers (A) and (B) should preferably have a molecular weight in the range of 15,000 to 150,000, more preferably 20,000 to 70,000. If the molecular weights of the copolymers are too small, the strength of the coating is diminished, whereas, if the molecular weight is too great, the tackiness of the composition to the tooth surface is reduced. Furthermore, the copolymers used in the present invention may contain vinyl alcohol formed by the hydrolysis of a portion of the vinyl acetate and may also contain small amounts (up to 10% by weight per 100 parts by weight of the vinyl chloride plus vinyl acetates units) of vinyl esters other than vinyl acetate.

In the method of the present invention, the polymer is applied as an organic solvent solution. Suitable dentally acceptable organic solvents have a boiling point of 140° C. or below and are essentially harmless to the human body. Examples of such solvents include acetone, methyl ethyl ketone, diethyl ether, diisopropyl ether, ethanol, n-propanol, isopropanol, tetrahydrofuran, methyl acetate, ethyl acetate, n-propyl acetate, isopropyl acetate, n-butyl acetate, isobutyl acetate, methylene chloride, ethylene chloride, chloroform, carbon tetrachloride, 1,1,1-trichloroethane, 1,1,2-trichloroethane, 1,1,1,2-tetrachloroethane, 1,1,2,2-tetrachloroethane, cyclohexane, toluene, ethylene glycol monomethyl ether, ethylene glycol monoethyl ether and the like. The solvents may be used either alone or as mixtures of two or more solvent materials. Of the solvents, acetone, diethyl ether, diisopropyl ether, ethanol, ethyl acetate, n-propyl acetate, isopropyl acetate, n-butyl acetate, isobutyl acetate, methylene chloride, ethylene chloride and chloroform are preferably employed. The polymer is dissolved in the solvent or solvent combination in a concentration of 1–20% by weight, preferably 5–15% by weight and is applied to tooth surfaces.

In the present invention the varnish preferably also contains a silane coupling agent which has an affinity with hydroxyapatite on tooth surfaces in order to further enhance the tackiness between the applied polymer and the tooth surface. Suitable examples of such a silane coupling agent include di- and trialkoxysilane compounds such as vinyltriethoxysilane, vinyltris($\beta$-methoxyethoxy)silane, $\gamma$-glycidoxypropyltrimethoxysilane, $\gamma$-methacryloxypropyltrimethoxysilane, N-$\beta$(aminoethyl)$\gamma$-aminopropyltrimethoxysilane, N-$\beta$(aminoethyl)$\gamma$-aminopropylmethyldimethoxysilane, $\gamma$-ureidopropyltriethoxysilane, $\gamma$-chloropropyltrimethoxysilane, $\gamma$-mercaptopropyltrimethoxysilane, $\beta$-(3,4-epoxycyclohexyl)ethyl-trimethoxysilane, and the like. The silane coupling agent is preferably added in an amount of 0–20% by weight, more preferably 3–10% by weight, based on the polymer. If the amount of the silane coupling agent added is too much, the strength of the coating is reduced.

In a preferred embodiment of the invention a dye is added to the varnish to color it. The coloring of the varnish is helpful in tooth restoration in that, after the varnish has been applied to a tooth surface, the caries portion is removed and the cavity is filled with a composite resin. If the varnish is colored, it clearly indicates the boundary between the protected tooth surface (healthy portion) and the portion to be filled and helps the dentist or dental technician to fill the resin in conformity to the shape of the cavity by being able to more clearly see where to remove excess applied resin. The dyes which are preferred are those which are essentially harmless to the human body. Cosmetic dyes which are sparingly soluble in water and soluble in organic solvents are preferably employed. Suitable examples of such dyes include Sudan III (Red No. 225), Rhodamine B Acetate (Red No. 214), Indigo (Blue No. 201), Sudan Blue B (Blue No. 403), Phthalocyanine Blue (Blue No. 404) and the like. In addition, inorganic pigments such as carbon black, iron oxide, chromium oxide and the like may also be employed. The dye is added to the varnish in an amount of 0.01 to 2% by weight based on the total liquid weight.

The varnish composed as described above for tooth protection is used in the restoration of teeth as follows: Initially, the varnish is applied to the surface of a tooth which requires restoration and the solvent is evaporated thereby forming a coating of polymer on the tooth surface. The solvent is preferably evaporated by blowing air over the applied polymer, and the thickness of the coating formed on the tooth surface is generally 1–10$\mu$ or so. Thereafter, the caries portion is removed by drilling, and then the surfaces of the cavity to be filled are treated with an acid etching agent. Since the healthy tooth surface is covered with the varnish of the present invention, when the acid etching agent is applied, it does not spread over the healthy tooth surface. After the acid etching treatment, the cavity is prepared for filling by coating the surfaces with a bonding agent containing an adhesive monomer, and thereafter the cavity is filled with resin. In the filling of the cavity, the composite resin must conform to the shape of the cavity, particularly in the case of molars. If the varnish is colored, the boundary between healthy tooth surfaces and the filled resin can be clearly observed, and this substantially facilitates the tooth restoration treatment. After completion of the restoration, the varnish is scraped off of the healthy tooth surfaces by an appropriate dental tool. In an alternative process, it is also possible to remove the caries portion by drilling and then coating the healthy tooth surfaces with the varnish of the present invention. (This must be done carefully or else the varnish will enter into the prepared cavity) Thereafter, the surfaces of the cavity are treated with the acid etching agent.

In the above process, the removal of the caries portion of a tooth by drilling, the acid etching treatment, the application of the bonding agent, and the filling of the dental filling material are each done in the conventional manner. Examples of the acid etching agent which may be used include those described in J. Dent. Res., 34, 849 (1955) and Japanese Patent application Laid-open 36994/1978. The bonding agent which is used is exemplified in, e.g., U.S. Pat. No 4,148,988, 4,182,035, 4,222,780, 4,259,075 and 4,259,117 and, the dental filling material used is the likes of those described in U.S. Pat. Nos. 3,926,906, 4,302,381, and 4,347,174.

As described hereinabove, since the present varnish for protecting tooth surfaces which comprises a vinyl chloride - vinyl acetate copolymer exhibits not only excellent tackiness to the tooth surface consisting of enamel, but also good strength, the healthy tooth surfaces may be protected from erosion by an acid etching agent during a tooth restoration treatment even when removing the caries portion by drilling after covering the tooth surface with the varnish, and then conducting the acid etching treatment. The present invention represents a significant contribution to this type of dental treatment.

Having generally described this invention, a further understanding can be obtained by reference to certain specific examples which are provided herein for purposes of illustration only and are not intended to be limiting unless otherwise specified.

EXAMPLE 1

Varnishes having the respective compositions set forth in Table 1 were prepared, and the tackiness of each varnish to a tooth surface was evaluated by applying the varnish to an extracted human tooth. The application of each varnish to tooth surfaces was conducted as follows: The tooth surface was cleaned with ethanol, and dried by exposure to a stream of air. Each varnish was applied to tooth surfaces from a sponge impregnated with a varnish. The solvent was evaporated using an air gun, and a tooth cavity (the size of the cavity being 3–4 mm in diameter) was formed in the center of the tooth surface covered with the coating using an air turbine (a carbide bar). The tackiness of the coating to the tooth surfaces after the tooth cavity was prepared was evaluated by visual observation, and also by the degree of penetration into the dyed coating of a drop of India ink dropped on the tooth surface. The results are presented in Table 1.

TABLE 1

| No. | 1 | 2 | 3 | 4 | 5 | 6 | 7 | Comparative |
|---|---|---|---|---|---|---|---|---|
| Composition (parts by weight) | | | | | | | | |
| Polymer (A) | 10.0 | 9.5 | 8.5 | 9.0 | 8.5 | 8.0 | 8.0 | — |
| Polymer (B) | — | — | 1.5 | 0.5 | 1.5 | 2.0 | 1.0 | — |
| Polymer (C) | — | — | — | — | — | — | — | 10.0 |
| Silane Treating Agent (M) | — | — | — | 0.5 | 0.5 | — | — | — |
| Silane Treating Agent (N) | — | 0.5 | — | — | — | 0.5 | 1.0 | — |
| Solvent (X) | 90.0 | — | 90.0 | 90.0 | 89.5 | 89.5 | — | — |
| Solvent (Y) | — | 90.0 | — | — | — | — | 90.0 | — |
| Solvent (Z) | — | — | — | — | — | — | — | 90.0 |
| Tackiness | A | A | AA | AA | AAA | AAA | AAA | B |

Note 1 Respective components
Polymer (A): Vinyl chloride - Vinyl acetate (80:20 mole %) copolymer M.W. 60,000
Polymer (B): Vinyl chloride - vinyl acetate - maleic anhydride (85:10:5 mole %) copolymer, M.W. 50,000
Polymer (C): Polyvinyl chloride
Silane treating agent (M): γ-Methacryloxy-propyltrimethoxysilane
Silane treating agent (N): Vinyltriethoxysilane
Solvent (X): Ethyl acetate - n-butyl acetate (80:20% by weight)
Solvent (Y): Ethyl acetate - acetone (70:30% by weight)
Solvent (Z): Dichloromethane
Note 2 Evaluation of Tackiness
AAA: The tackiness to the tooth surface is very good. (The condition of the coating after the tooth cavity preparation is good.)
AA: The tackiness to the tooth surface is good. (The condition of the coating after the tooth cavity preparation is good.)
A: The tackiness to the tooth surface is moderate. (A part of the coating has detached from the tooth surface, but the rest remains adherent to the tooth surface.)
B: The tackiness to the tooth surface is poor. (The greater part of the coating has detached from the tooth surface.)

As is evident from Table 1, with the varnishes within the scope of the present invention, the same exhibited tackiness to the tooth surfaces. Especially, where polymers were used which contained maleic anhydride as a component were employed, and further where the silane coupling agents were each added, it was observed that excellent tackiness to the tooth surfaces was exhibited.

EXAMPLE 2

A tooth restoration was conducted utilizing the varnish No. 5 identified in Table 1, which was prepared by adding 0.5% by weight, based on the total weight of varnish, of Phthalocyanine Blue. A sponge was impregnated with the varnish and the same was applied to the surface of a molar tooth having a caries. The tooth surface was dried using an air gun, thereby forming a polymer coating. After the formation of the coating, the caries portion was removed using a drill while being guided by the carious detector disclosed in U.S. Pat. No. 4,347,233 to form a class 2 cavity. The coating which adhered to the healthy tooth surface was stable even after the formation of the tooth cavity. Thereafter, a 40% aqueous phosphoric acid solution was applied to the wall of the tooth cavity and dried, after which a bonding agent (commercial name: Clearfil Posterior) was applied to the wall of the tooth cavity and dried. Thereafter, the tooth cavity was filled with the composite resin of the Clearfil Posterior product along the outer line of the colored coating on the tooth crown and hardened. Thus, the caries tooth was treated, and since the tooth surface was protected with the varnish of this invention, spreading of the acid etching agent over to healthy tooth surfaces was not observed. Further, the composite resin which had flowed over from the tooth cavity at the time of restoring the tooth had to be removed from the tooth surface. However, since the coating was colored, it was easy to distinguish the tooth surface from the composite resin, and it was possible to easily remove the excess resin. After restoration, it was possible to remove the colored coating by simple scraping.

EXAMPLE 3

An enamel caries showing a slight chalk color on a molar occlusal surface was cut and removed using a drill to form a tooth cavity. Thereafter, a varnish having the composition referred to as No. 6 in Table 1 and colored further by adding thereto 0.5% by weight, based on the total liquid weight, of Phthalocyanine Blue (dye), was applied carefully to the periphery of the tooth cavity using a piece of impregnated sponge to prevent the varnish from running into the inner portion of the cavity, and the tooth surface was gently dried using an air gun to form a coating. After confirming that the coating did not sag into the inner portion of the cavity, a 40% aqueous phosphoric acid solution was applied to the entire tooth cavity, then bonding agent was applied to the cavity surface and dried. Thereafter, the tooth cavity was filled with a composite resin and hardened. The resin which overflowed from the tooth cavity was scraped off using a finish polishing bar while resorting to the blue-colored coating present beneath the resin as a guide until the blue coating had been completely removed. Thus, where the coloration of the caries was small as in this case, by applying the varnish after forming the tooth cavity, restoration was successfully conducted while protecting the healthy enamel against the acid treatment.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method for restoring a carious tooth and protecting healthy tooth surfaces against erosion by an acid etching solution, which comprises:
   (i) applying a polymer solution to the tooth surface, and evaporating the solvent from said solution to form a polymer coating on the surface;
   (ii) removing the carious portion of the tooth by drilling;
   (iii) applying an acid etching agent to the walls of the tooth cavity from which the carious material has been removed;
   (iv) thereafter, filling the tooth cavity with a dental filling material; and
   (v) removing the polymer coating from the healthy tooth surfaces.

2. The method of claim 1, wherein the polymer solution is a solution of a polymer primarily comprising vinyl chloride and vinyl acetate monomer units dissolved in a solvent.

3. The method of claim 2, wherein said polymer is a mixture of a copolymer (A) of (a) vinyl chloride and (b) vinyl acetate and a copolymer (B) of (a) vinyl chloride, (b) vinyl acetate, and (c) a vinyl compound having a carboxylic acid or carboxylic acid anhydride group or groups.

4. The method of claim 3, wherein in said copolymers (A) and (B), the relative amounts of monomers (a) and (b) are 95–60 and 5–40 mole %.

5. The method of claim 3, wherein in said copolymer (B), the amount of component (c) relative to components (a) and (b) ranges from 1–20 mole %.

6. The method of claim 3, wherein the relative amounts of copolymer (A) and copolymer (B) in said mixture range from 95–40 and 5–60% by weight, respectively.

7. The method of claim 3, wherein the polymer solution further contains 3–10% by weight, based on the polymer, of a silane coupling agent which enhances the tackiness of the tooth surface protecting components to the tooth surface.

8. The method of claim 2, wherein the polymer solution further contains 0.01–2% by weight, based on the solution, of a dye so as to define the boundary between the portions of the tooth surface to be protected and the tooth portion to be restored.

9. The method of claim 12, wherein the concentration of the total copolymers in the polymer solution is 1–20% by weight.

10. The method of claim 12, wherein said solvent is a compound selected from the group consisting of acetone, diethyl ether, diisopropyl ether, ethanol, ethyl acetate, n-propyl acetate, isopropyl acetate, n-butyl acetate, isobutyl acetate, methylene chloride, ethylene chloride, chloroform, or a mixture of two or more such compounds.

11. A method for restoring a carious tooth and protecting healthy tooth surfaces against erosion by an acid etching solution, which comprises:
   (i) removing the caries portion of the tooth by drilling;
   (ii) applying a polymer solution to the remaining healthy surfaces of the tooth and evaporating the solvent from said solution thereby forming a polymer coating on the healthy tooth surfaces;
   (iii) applying an acid etching agent to the walls of the tooth cavity from which the carious portion has been removed;
   (iv) filling the treated tooth cavity with a dental filling material; and
   (v) removing the polymer coating from the healthy tooth surfaces.

* * * * *

UNITED STATES PATENT AND TRADEMARK OFFICE
CERTIFICATE OF CORRECTION

PATENT NO. : 4,443,197
DATED : April 17, 1984
INVENTOR(S) : Takao Fusayama and Junichi Yamauchi It is certified that error appears in the above-identified patent and that said Letters Patent is hereby corrected as shown below:

Column 8, line 13, delete "3" and insert therefor:

--2--.

Column 8, line 23, delete "12" and insert therefor:

--2--.

Column 8, line 26, delete "12" and insert therefor:

--2--.

Signed and Sealed this

Thirtieth Day of April 1985

[SEAL]

Attest:

DONALD J. QUIGG

Attesting Officer   Acting Commissioner of Patents and Trademarks